United States Patent
Hall

(10) Patent No.: US 9,974,995 B2
(45) Date of Patent: May 22, 2018

(54) PERFECT POWER ROWING ERGOMETER HANDLE

(71) Applicant: Michael Sean Hall, Philadelphia, PA (US)

(72) Inventor: Michael Sean Hall, Philadelphia, PA (US)

(73) Assignee: Michael Sean Hall, Philadelphia, PA (US)

(*) Notice: Subject to any disclaimer, the term of this patent is extended or adjusted under 35 U.S.C. 154(b) by 17 days.

(21) Appl. No.: 15/209,656

(22) Filed: Jul. 13, 2016

(65) Prior Publication Data

US 2017/0014669 A1    Jan. 19, 2017

Related U.S. Application Data

(60) Provisional application No. 62/191,842, filed on Jul. 13, 2015.

(51) Int. Cl.
*A63B 24/00* (2006.01)
*A63B 21/00* (2006.01)
(Continued)

(52) U.S. Cl.
CPC ...... *A63B 21/4035* (2015.10); *A63B 22/0076* (2013.01); *A63B 22/0087* (2013.01); *G06F 19/3481* (2013.01); *A63B 71/0622* (2013.01); *A63B 2022/0079* (2013.01); *A63B 2071/065* (2013.01); *A63B 2220/17* (2013.01); *A63B 2220/20* (2013.01); *A63B 2220/30* (2013.01); *A63B 2220/40* (2013.01);
(Continued)

(58) Field of Classification Search
CPC ............ A63B 22/0076; A63B 22/0087; A63B 21/4035; A63B 2022/0079; A63B 2220/51; A63B 2220/40; A63B 2220/20; A63B 2220/30; A63B 2220/17; A63B 2220/64; A63B 2225/50; A63B 2230/00; A63B 2230/06; A63B 2230/08; A63B 2071/0622; A63B 2071/065
See application file for complete search history.

(56) References Cited

U.S. PATENT DOCUMENTS

| | | | | |
|---|---|---|---|---|
| 4,674,741 A | * | 6/1987 | Pasierb, Jr. | ..........  A63B 21/153 482/6 |
| 4,757,988 A | * | 7/1988 | Szymski | ..............  A63B 21/157 482/59 |

(Continued)

*Primary Examiner* — Glenn Richman

(57) ABSTRACT

A replacement handle for rowing exercise machines. The rowing machine handle described herein is a simple tool which can be added to existing machines to give the user greater feedback and control over training and exercise sessions, on a variety of rowing exercise machines, than is currently available. It is easy to use, and with included applications for mobile devices will help the user to create more effective training sessions and training programs. Said rowing machine handle can be used effectively by a wide range of users. Current rowing machine handles do not provide electronic feedback about the rowing motion or exercise performance. The above replacement handle will provide direct and immediate feedback to the user about his exercise session, including information about his rowing motion (technique) and his exercise performance (physiology).

5 Claims, 3 Drawing Sheets

(51) Int. Cl.
*A63B 22/00* (2006.01)
*G06F 19/00* (2018.01)
*A63B 71/06* (2006.01)

(52) U.S. Cl.
CPC ....... *A63B 2220/51* (2013.01); *A63B 2220/64* (2013.01); *A63B 2225/50* (2013.01); *A63B 2230/00* (2013.01); *A63B 2230/06* (2013.01); *A63B 2230/08* (2013.01); *A63B 2230/20* (2013.01)

(56) References Cited

U.S. PATENT DOCUMENTS

| | | | | |
|---|---|---|---|---|
| 4,984,986 | A | * | 1/1991 | Vohnout ................. A63B 24/00 434/247 |
| 5,072,929 | A | * | 12/1991 | Peterson ............ A63B 22/0076 310/105 |
| 2014/0038779 | A1 | * | 2/2014 | Zuckerman ............ A63B 69/10 482/8 |
| 2016/0375297 | A1 | * | 12/2016 | Kiser ................. A63B 22/0076 482/73 |

\* cited by examiner

PERFECT POWER ROWING ERGOMETER HANDLE

This application is a non-provisional application of provisional app No. 62/191,842, filed on Jul. 13, 2015.

BACKGROUND OF THE PRESENT INVENTION

Field of the Invention

The present invention relates to the handle of a rowing exercise machine (a.k.a. rowing ergometer) with the dual function of a) replacing the original, manufacturer-provided handle, and b) providing electronic feedback on various parameters of each exercise session.

Description of Related Arts

A rowing machine is an exercise machine meant to replicate or resemble the motions produced in the sport of rowing on the water. It is also an alternative exercise to rowing on the water. The sport of rowing is unique and specific in its motion, intensity, and types of utilized boating equipment when compared to other types of rowing boats. It is not to be confused with kayaking or canoeing, or other paddle boating activities. A rowing machine is a whole body exercise device configured to consume a substantial amount of energy within a short period of time, by mimicking the physical motions carried out in rowing boats on the water. It is designed to actively produce similar rowing rhythms and feelings to a user using the rowing machine. During use, the user sits on the seat of the machine (usually a reciprocating seat on a rail) facing the body of the machine. He secures his feet to the footplate which is attached to the machine, usually with straps that are connected to the footplate. He then takes the handle of the machine in his hands and begins exercise. Unlike stepper or running machines which focus on mainly lower body muscle groups, the rowing machine is very effective for performing whole-body exercise. In some cases where the rowing machine is provided with a display unit (also referred to as monitor), the exercise results can be recorded and stored through the monitor and a storage device, while the exercise is being monitored in real time. The rowing machine is well known throughout the world, and some rowing machine products are capable of performing head-to-head or on-line racing through local area connection, or through the Internet with other areas or countries. The rowing machine does not generate significant noise levels and is light in weight, and can be used and stored indoors.

The rowing machine is frequently used by athletes in many countries for training, and, since the exercise is performed while the user is sitting in the seat as mentioned above, the rowing machine is often used for physical therapy purposes as well.

Referring to FIGS. 1A and B and FIG. 2, an operating method of the rowing machine is described. A user sits in a seat capable of reciprocally moving in forward and backward directions on a rail connected to the body of the rowing machine, and facing the body of the rowing machine, then places the soles of the feet on footboards. Next, he takes a handle of the rowing machine in both hands. Starting from a forward position, in the direction he is facing, with the legs comfortably compressed, arms extended, and torso bent slightly forward from the waist (FIG. 1A), the user applies a given force to his feet on the footboards from the legs, and at the same time, he extends or opens his torso backwardly, and draws the arms and hands to the chest (FIG. 1B), so as to pull the handle toward his chest by using the force generated from his legs, back and arms. At this time, his knees and legs are fully extended, and the reciprocally moving seat has been moved to the rear of the rail. This state is maintained briefly after the pulling operation so as to allow his muscles to be sufficiently contracted. After that, if the force applied from his legs, back and arms is removed, the handle is moved back to its original position by means of reversing the previous motions. At this time, his back and waist are bent in a forward direction, and the arms are extended forward. Also, the seat is moved forward, so that his knees are bent to return to the initial state of the rowing operation (FIG. 1A). The rowing operation is repeatedly carried out to obtain whole body exercise effects.

Through the repetition of the above-mentioned rowing operations, the muscles of the user's back, arms, shoulders and lower body are strengthened, and aerobic and anaerobic exercise for the user's whole body is performed, so that the rowing machine can be used for training purposes for amateur and professional athletes, as well as for therapeutic purposes for disabled persons (caused either by birth or by unexpected accidents).

As aforementioned, many rowing machines are equipped with monitors which display, store, and recall various exercise result data. Information typically collected by rowing machine monitors includes: elapsed time; stroke rate (displayed as strokes per minute); speed (displayed as time/500 meters); elapsed and/or accumulated distance covered; projected time to finish, watts per hour; calories per hour; and accumulated calories spent. For most uses, the displayed information is sufficient for effective training to be carried out, however most monitor units do not display, in a useful form, the real-time force output during the exertion stage of the rowing operation. Information on force output is a key aspect of certain types of specific training, and in particular, strength-gaining exercises. In addition to this missing information is the missing ability to monitor, store, and recall said force output.

Technical Problem

Accordingly, the present invention has been made in view of the aforementioned problems occurring in the prior art, and it is an object of the present invention to provide a rowing machine replacement device that is configured to have a handle of a rowing machine adapted to sense, measure and transmit said applied force during exercise.

Technical Solution

To accomplish the above object, according to the present invention as shown in FIG. 3, there is provided a rowing machine replacement handle device (FIG. 3) including: a main framework (A) of similar size, shape, and material as existing rowing machine handles; grips (B) covering either end of said main framework; connection point (C) with interchangeable parts to allow connection to the various rowing exercise machines; spaces for internal electronic or mechanical components (D) embedded within said main framework. The internal electronic and/or mechanical components included within the main framework include: a mechanism for measuring force (E) applied to said handle when in use; a mechanism for measuring distance (F) traveled by said handle when in use; a mechanism for measuring relative changes in height (G) of said handle when in use; a mechanism for measuring rate of stroking (H) when said handle is in use; a circuit board (J) with processor (M) for gathering, collating, and converting information from above components to a transmittable and readable format. Said circuit board also includes a component (L) for wirelessly transmitting gathered data to outside receivers; a power source (K) to power above components as needed; wiring (N) to connect above components and power source.

According to the present invention, the original manufacturer-provided rowing machine handle is removed from the rowing machine, and replaced with the replacement handle device above via the connection point. The user then powers on the replacement handle device and wirelessly connects it to a user-provided receiver (i.e. mobile device, laptop computer, tablet device). Proprietary software provided with the present invention will receive, convert, and display the various measurements collected by the present invention. The user then proceeds to use the rowing machine in the normal fashion, as recommended by manufacturer and described above.

According to the present invention, when the unit is powered on, performance data will be continuously collected from all internal components, electrical and mechanical, within said rowing machine handle device, by the internal processor component where it is collated and converted to a transmittable format. The information is then sent to the wireless transmitting component where it is immediately transmitted to any connected outside device. If the connected device is running the proprietary application or program, the transmitted information will be displayed on the screen of the connected device, in real-time, in a visual display format the user can easily and readily comprehend. This instant data feedback provided by the above invention may then be used to immediately alter or adjust the user's exercise motion and/or intensity, as deemed appropriate or necessary by the user. The feedback data from the above invention may also be stored on the connected device, wherever possible, for later review.

In the case that the above replacement handle is not powered on, it may continue to be used as a normal handle for the rowing machine.

In the case the user wishes to replace the present invention with the original manufacturer-provided handle, or other device, the present invention will easily detach via the connection point, and may then be replaced with the original handle or other device. The present invention may subsequently be reattached, as needed by the user. The present invention is not a permanent fixture addition to any rowing exercise machine.

In the case that new technology makes further physiological measurements possible by using the present invention (i.e. heart rate monitor or lactate measuring device), such technology will be incorporated into the present invention, as space allows.

Advantageous Effects

According to the present invention, and as mentioned above, the added effect of utilizing said replacement rowing machine handle is the addition of new information feedback to the user in real time, during use. This information gives the user greater knowledge of the exercise he is currently engaged in. The user can use this information to thus improve various physiological and technical aspects of his performance. Access to stored data from exercise sessions offers the user the ability to more fully examine the various aspects of performance, and hence create strategies to improve performance in the future by directly identifying specific strengths and weaknesses in the rowing motion and/or physiological performance.

DESCRIPTION OF DRAWINGS

The preferred embodiments of the present invention are specifically illustrated in the drawings, in such a manner that the above objects, characteristics, and advantages of the present invention become clearer. Same letter designations in the drawings refer to the same elements listed below. The drawings are deliberately not drawn in a uniform scale according to the actual scaling. The emphasis of the drawings is to show a purport of the present invention.

FIGS. 1A and 1B are side views showing operating methods of a conventional rowing machine, wherein FIG. 1A shows an initial state before force is applied to the rowing machine and FIG. 1B shows the final position after force has been applied.

FIG. 3 is a cross-sectional overhead view of the above invention, where the body of the rowing machine would be to the left of drawing, and showing approximate number and placements of the elements included in the preferred embodiment. These elements, listed below, are referenced in FIG. 3, wherein

DETAILED DESCRIPTION OF THE INVENTION

A is the main framework of the invention, with removable end caps, and to or within which the below elements are attached or embedded.

B are non-slip grips attached to either end of the handle, each of which is of sufficient length to accommodate a hand of any size and width, at various placements.

C is an interchangeable connector or joint to accommodate the various rowing machines, to which the chain, belt, cable, or other pulling mechanism is connected.

D are the spaces within the handle framework which will accommodate the electronic and mechanical elements of the invention.

E is a load cell or other force-measuring device which will measure force applied to the handle through the connector C via the chain, belt or cable of the rowing machine, when in use.

F, G, and H are electronic devices, such as accelerometers, used to measure handle movement so as to extrapolate accurate information about distance traveled by the handle over the course of a single repetition of the rowing motion, handle position within said repetition, handle height during said repetition, frequency of repetitions, and other data inputs the inventor may wish to add, as the technology allows.

J is the circuit board for collating and processing (M), then transmitting (L) information gathered by the above elements when in use.

K is the power source, typically a replaceable or rechargeable battery, for powering the above elements included within the invention.

L is an electronic device, such as Bluetooth, for transmitting collected data to an external display or device.

M is the electronic processing device for collecting and collating data, and communicating with all internal electronic components.

N is the wiring to connect all embedded elements together for, power and information transmission.

Figure 1A:
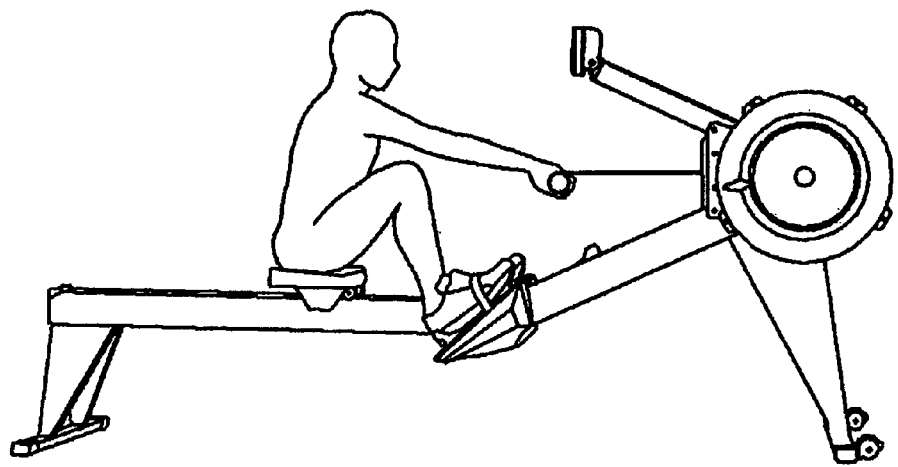
Figure 1B:
Figure 1B:
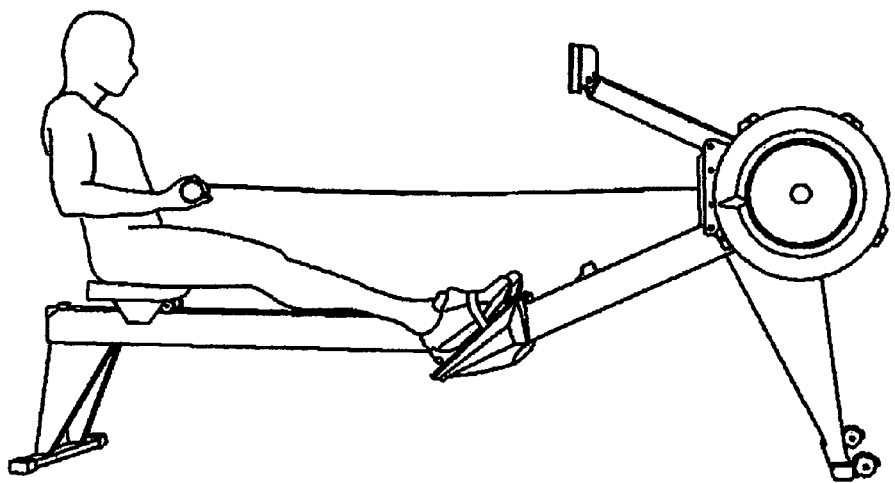
Figure 2:
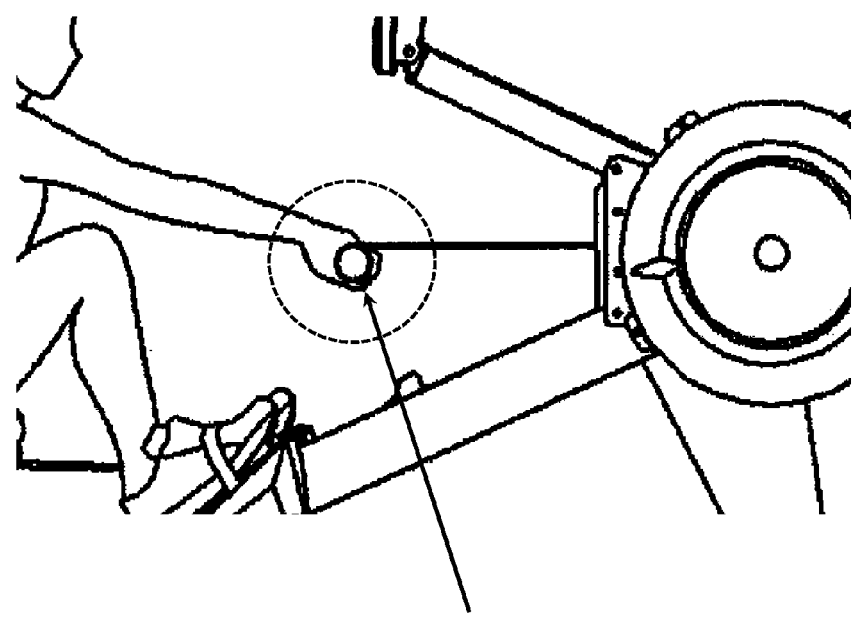
FIG. 2 is a close-up view with an arrow indicating a typical handle (shown in profile) held in the hands of the rowing figure.
Figure 3:
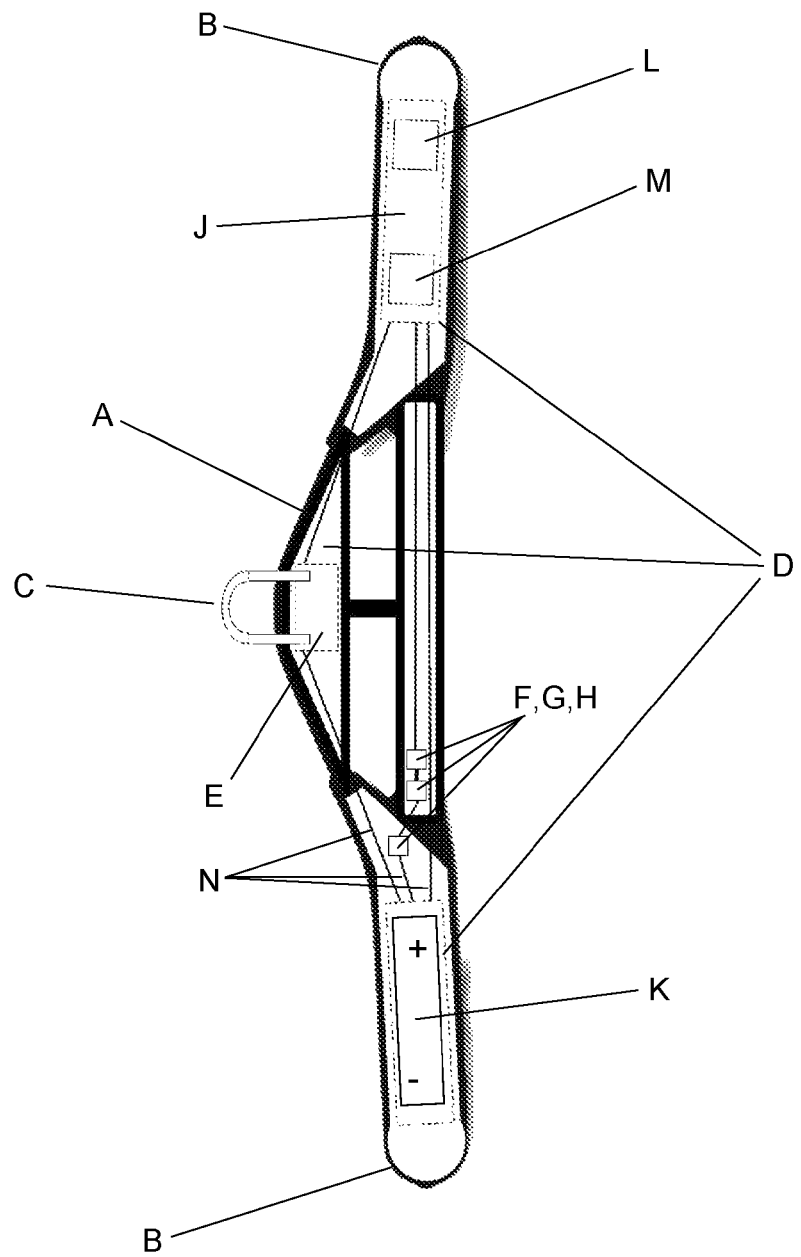

Placements of the above elements and embedded spaces may change relative to each other in FIG. 3.

What is claimed is:

1. A rowing machine handle, comprising
a central framework with handle portions extending at either end of the central framework;
internal electrical components within the handle for measuring applied force;
internal electrical components within the handle for measuring handle movement;
internal electrical components within the handle for collecting data input from the internal electrical measuring components;
internal electrical components within the handle for transmitting collected data to an external electrical display;
internal power source within the handle for the internal electrical components;
internal wiring within the handle to connect various internal electrical components;
a connector on the handle to enable handle to be attachable to and detachable from and used with various rowing machines; and
handle grips on the handle portions; wherein the handle portions are hollow cylindrical handle portions at either end of and rigidly secured to a central triangular framework; and a metal connector at the apex of the triangular framework.

2. A rowing machine handle in accordance with claim 1, wherein the handle is attachable to and detachable from a rowing machine by a chain, cable or belt attachable to or detachable from the connector on the handle.

3. A rowing machine handle in accordance with claim 1, the handle further incorporating a hollow portion between the handle portions encompassing at least a portion of the central triangular framework, the hollow portion and the hollow handle portions each enclosing internal spaces:

a force measuring device secured within the internal space of the hollow portion to the framework and connecting to the metal connector for collecting data corresponding to the force applied to the handle; and within at least one of the internal spaces:

a device for measuring and collecting data corresponding to speed, position, distance traveled, and relative fluctuations thereof;
a transmitter for transmitting the data collected by the devices for measuring and collecting the data corresponding to the force, speed, position, distance traveled and relative fluctuations thereof to an external display;
a programmable computer to communicate with all internal electrical components, collate the collected data, and convert the data to a transmittable form to be interpreted and displayed by an existing external device with display capabilities;
a transmitter for transmitting the data collected by the devices and interpreted by the programmable computer to an external display;
a circuit board to mount the computer, transmitter and the devices for measuring and collecting the data corresponding to the force, speed, position, distance traveled and relative fluctuations thereof;
a power source to sufficiently power the internal electrical handle components; and
wiring to connect the power source to the components, the devices, the computer, and the components, devices and computer to each other as needed.

4. A rowing machine handle in accordance with claim 1, each of the hollow handle portions encompassing an internal space, further incorporating a removable end cap at an end of each handle portion to allow access to the internal spaces and components within each handle portion.

5. A rowing machine handle in accordance with claim 4, wherein the handles are covered with a removable grip.

\* \* \* \* \*